(12) United States Patent
Wagner et al.

(10) Patent No.: US 8,215,960 B2
(45) Date of Patent: Jul. 10, 2012

(54) WATER AND SODIUM HYPOCHLORITE INDICATING ENDODONTIC MONITORING DEVICES

(75) Inventors: Jeffrey A. Wagner, Salt Lake City, UT (US); Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 54 days.

(21) Appl. No.: 11/533,187

(22) Filed: Sep. 19, 2006

(65) Prior Publication Data

US 2008/0070194 A1    Mar. 20, 2008

(51) Int. Cl.
*A61C 5/02* (2006.01)

(52) U.S. Cl. ........................................ 433/224

(58) Field of Classification Search ................ 433/224, 433/81, 102; 106/35; 424/48–58, 435
See application file for complete search history.

(56) References Cited

U.S. PATENT DOCUMENTS

| | | | | |
|---|---|---|---|---|
| 4,428,872 | A * | 1/1984 | Callicott | 510/193 |
| 5,290,172 | A | 3/1994 | Sakuma et al. | 433/215 |
| 5,725,373 | A | 3/1998 | Yeh | 433/72 |
| 6,482,009 | B1 * | 11/2002 | Rubin | 433/224 |
| 6,559,351 | B1 | 5/2003 | Eakin | 602/56 |
| 6,576,473 | B1 | 6/2003 | Scaringe et al. | 436/169 |
| 2002/0081550 | A1 | 6/2002 | Karazivan | 433/80 |
| 2003/0008264 | A1 * | 1/2003 | Rubin | 433/224 |
| 2005/0112528 | A1 * | 5/2005 | Wagner et al. | 433/224 |
| 2005/0130253 | A1 * | 6/2005 | Lye et al. | 435/29 |
| 2007/0017413 | A1 * | 1/2007 | Kwan et al. | 106/31.09 |
| 2008/0057534 | A1 * | 3/2008 | Martin et al. | 435/34 |

FOREIGN PATENT DOCUMENTS

EP    0549633    7/1997

OTHER PUBLICATIONS

Dtsch Zahnarzt Z., 45(4): 222-6 1991 "Drying of Root Canals" Database: PubMed, Accesseion No. 91078238.

* cited by examiner

*Primary Examiner* — Sunil K Singh
(74) *Attorney, Agent, or Firm* — Workman Nydegger

(57) ABSTRACT

Water and aqueous sodium hypochlorite indicating endodontic monitoring devices include a cone-shaped water absorptive material and color changing system applied thereto that selectively changes to different colors when exposed to either water or aqueous sodium hypochlorite within a root canal chamber. The devices include a pH changing material, pH indicator, and pH insensitive dye. The dye imparts an initial color when the device is dry. The pH changing material and pH indicator react with water to yield a second color. In the presence of aqueous sodium hypochlorite, the device changes to a third color different from the initial color and second color as a result of bleaching the dye and/or pH indicator. Color changing devices are manufactured by applying an aqueous solution that includes a pH changing material and dye to a water absorptive cone, drying the cone, applying an anhydrous pH indicator solution, and then drying the cone again.

17 Claims, 2 Drawing Sheets

WATER AND SODIUM HYPOCHLORITE INDICATING ENDODONTIC MONITORING DEVICES

BACKGROUND OF THE INVENTION

1. The Field of the Invention

The present invention relates to endodontics devices, more particularly to a device and method for easily determining whether moisture and/or aqueous sodium hypochlorite is present within the root canal of a tooth prior to sealing the root canal.

2. The Relevant Technology

When a dental practitioner performs a root canal, pulp and other material in the root canal chamber is removed. This is typically performed using one or more abrading endodontic files. Soft pulp material can be further broken up, disinfected and washed out using aqueous sodium hypochlorite. The sodium hypochlorite and any remaining debris can by flushed out by irrigating with water.

Once a dentist has removed diseased and soft tissue from a tooth's root canal, the chamber is typically filled. Before the canal can be filled with gutta percha, sealant or other suitable material, any moisture present within the canal is advantageously removed. It is beneficial to remove the moisture, which can otherwise result in bacterial infection of the chamber. Moisture can also inhibit bonding between the root canal walls and a sealant, if used. In some instances, pressurized air has been used to dry the canal, but because the source of pressurized air often contains moisture that can condense in the canal, use of this method has been discouraged. Dental practitioners have attempted to dry the canal by using cotton swabs or paper points which can be inserted down into the canal. Because of the relatively large size of cotton swabs and the narrow cross sections of the canals, especially in the apical region, complete removal of all moisture may prove difficult. Paper points are more easily inserted into the canal and are especially useful as they are able to extend through curved and narrow portions of the canal. Nevertheless, it may be difficult to determine whether all the moisture has been removed from the canal by visual inspection alone. One way to determine whether there is moisture in the root canal is to cause a paper point to change color in the presence of moisture. U.S. Pat. No. 6,482,009 to Rubin discloses an implement that includes a tip treated with a pH indicator. The problem with color changing pH indicators is that this typically only changes color within a specific working range of the pH scale. When a pH indicator is exposed to a pH outside the working range for that pH indicator, little or no color change may occur. Thus, the device of Rubin cannot guarantee a substantial color change, even if water is present, unless the pH in the root canal also happens to be within the applicable pH range of the indicator. Moreover, if there is sodium hypochlorite present in the root canal, the indicator of Rubin may never change color if it is entirely bleached away, providing a false negative.

A more reliable way to detect both moisture and sodium hypochlorite is provided in U.S. Publication No. 2005/0112528 to Wagner et al. In this application, a cobalt salt is provided that changes to one definitive color when exposed to moisture, regardless of pH, and to a different color when exposed to sodium hypochlorite. However, cobalt salts are disfavored in some places, including Europe, where they are believed to be carcinogenic or otherwise unhealthful. For this reason, warnings must typically be applied to products containing cobalt salts that are to be introduced into the mouth.

In view of the foregoing, it would be an improvement in the art to provide a device and method which may be used to safely and accurately determine and distinguish between whether moisture or aqueous sodium hypochlorite is present within a root canal.

BRIEF SUMMARY OF THE INVENTION

The present invention relates to an endodontic device that exhibits a first color when placed in a dry root canal, a second color when exposed to moisture within the root canal, and a third color when exposed to aqueous sodium hypochlorite in the root canal in order to detect the presence of moisture and/or hypochlorite within a root canal and accurately distinguish between the two. When the practitioner abrades and cleans the pulp tissue from the root canal, sodium hypochlorite may be introduced in order to disinfect the canal prior to drying and eventually sealing the canal. The sodium hypochlorite can then be rinsed out with water. The endodontic device of the present invention changes to a different color when exposed to aqueous sodium hypochlorite than when exposed to moisture, thus permitting the practitioner to be certain that the aqueous sodium hypochlorite has been flushed or otherwise removed from the root canal chamber.

The inventive water and sodium hypochlorite detecting devices according to the invention comprise an endodontic cone or other elongate device insertable into a root canal formed of a water absorptive material, a pH indicator that changes color within a specified pH range, a pH changing material that ensures that moisture absorbed into the absorptive material is within the specified pH range to guarantee a color change when water is present, and a dye that is advantageously sensitive to sodium hypochlorite.

The endodontic cone may be formed of paper or other material that is water absorptive. The endodontic cone may be sprayed, dipped, or otherwise coated with the pH indicator, pH changing material, and dye. According to one embodiment, the pH changing material and dye may be applied to the absorptive material by means of a solvent that is then evaporated away to yield a dry intermediate product. The solvent may contain water so long as the water is removed from the absorptive material prior to applying the pH indicator in order to avoid premature reaction between the pH indicator and pH changing material. The pH indicator is typically applied using an anhydrous solvent to prevent such reaction.

In use, the device is inserted into the root canal of a patient's tooth. Because the device includes a dye, it initially exhibits a first color (e.g., blue in the case of a blue dye). If the root canal is dry, no color change is observed. If moisture is present within the root canal, the pH indicator (e.g., phenolphthalein) will change color (e.g., red) as the water causes a reaction between the pH indicator and the pH changing material. The color of the pH indicator will typically be different than the color of the dye in order to cause the endodontic device to change to a different color when exposed to water (e.g., purple in the case of red phenolphthalein and blue dye). If sodium hypochlorite is present in the root canal, at least one of the dye or indicator will be bleached out in order for the device to exhibit a different color (e.g., white in the case where both the dye and indicator are bleached away).

The endodontic devices of the invention alert the practitioner to the presence of moisture and/or sodium hypochlorite within the root canal and distinguishes between the two. If moisture is detected, the practitioner may insert additional moisture absorptive devices into the root canal until the root canal is dry. The practitioner will be alerted that the canal is dry when the inserted device does not change color. If sodium hypochlorite is detected, the practitioner can flush the root canal with water until the color change of a subsequently inserted device indicates the presence of water but not sodium hypochlorite. Additional moisture absorptive devices can be inserted into the root canal until the root canal is dry.

One of skill in the art will appreciate that the chemical mechanisms employed to detect the presence of moisture and/or sodium hypochlorite are entirely different than when a cobalt salt is used to detect moisture and/or sodium hypochlorite. The detection of moisture requires an initial interaction between water found in the root canal and the pH changing material of the endodontic device in order to alter the relative concentration of hydronium ions ($H_3O+$) to hydroxide ions ($OH-$) found in water to within the specified pH range of the pH indicator. When the pH of the water in the root canal has been adjusted to within the working pH, the range of the indicator pH indicator changes color. Thus, the color change indicating the presence of water is a pH sensitive reaction. Color changes involving a cobalt salt are insentive to pH and thus of a completely different chemical mechanism. The detection of sodium hypochlorite is subtractive in the sense that color that would otherwise be imparted by the dye and/or indicator is removed by a bleaching reaction involving hypochlorite ion and/or its aqueous analogs. Cobalt salts typically turn black when exposed to sodium hypochlorite. Since black is the composite of all colors, the chemical mechanism that turns cobalt salts black is the very opposite of a subtractive color change caused by bleaching.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

The present invention relates to a device for detecting the presence of moisture and sodium hypochlorite within a root canal chamber and distinguishing between the two. The device comprises an endodontic cone formed of a water absorptive material (e.g. paper) that includes a pH indicator, a pH changing material, and a dye applied to the water absorptive material. The pH indicator and pH changing material interact in the presence of water to effect a definitive color change, thereby detecting the existence of moisture within a root canal. In the presence of sodium hypochlorite, another color change occurs. Yet another color is exhibited if the root canal is dry.

II. Exemplary Device and Method of Manufacture

Figure 1A:
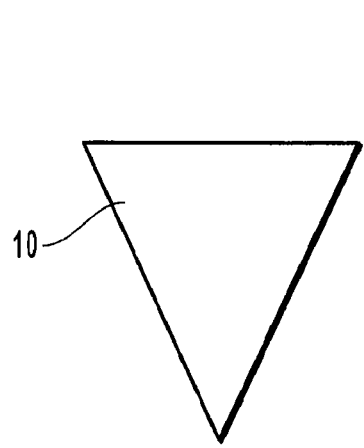
FIG. 1A is a perspective view of a piece of water absorptive material having a triangular shape.
Figure 1B:
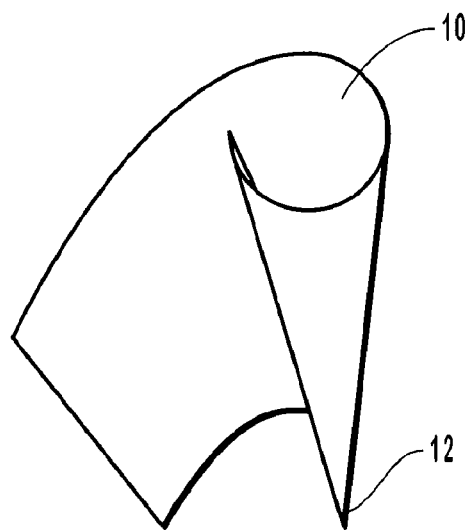
FIG. 1B is a perspective view of the water absorptive material of FIG. 1A, the material being partially rolled so as to form an endodontic cone.
Figure 2:
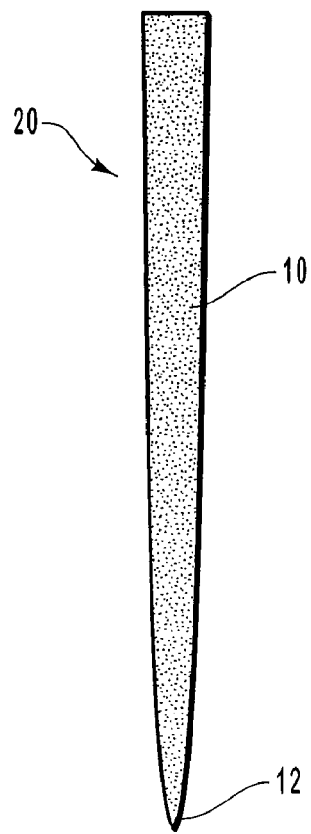
FIG. 2 is a perspective view of an exemplary device according to the present invention.

FIG. 1A is a perspective view of a piece of a water absorptive material 10, such as paper. The water absorptive material 10 is illustrated as having a generally triangular shape. FIG. 1B illustrates the water absorptive material 10 being rolled into a cone shape, having a tip 12 at one end, while FIG. 2 illustrates the water absorptive material 10 having been tightly rolled into an endodontic cone 20. The endodontic cone device 20, as illustrated in FIG. 2, comprises a water absorptive material 10 having a tip 12 and a color changing system applied to the water absorptive material. The color changing system includes a pH indicator that changes color within a specified pH range, a pH changing material that ensures that water that soaks into the device 20 has a pH within with the specified range, and a dye.

The color changing system is advantageously applied to the water absorptive material 10 in a manner that prevents a premature reaction between the pH indicator and the pH changing material. To prevent such a reaction, the two components are advantageously applied in a manner so that they are not contacted with water at the same time during manufacture of the device 20. In this way, the reaction between the pH indicator and pH changing material can be first triggered by moisture found in a root canal. Thus, one or both of the pH indicator and pH changing material is advantageously applied as an anhydrous solution or other dry form that is substantially free of water. Typically, the first material to be applied to the device 20 can be applied using either an aqueous or anhydrous solution, and the second material is applied as an anhydrous solution or other dry form to prevent premature reaction.

According to one embodiment, the pH changing component and dye of the color changing system may be applied first to the water absorptive material 10 as either an aqueous solution or an anhydrous solution using a non-water containing solvent system. The solution may include a wetting agent and/or a surfactant in addition to the water or other solvent and the color changing components. The pH changing component may be included in an amount ranging from about 0.01% to about 20% by weight, preferably about 0.05% to about 15% by weight, and more preferably about 0.1% to about 10% by weight of the solution. The dye component may be included in an amount ranging from about 0.0001% to about 2% by weight, preferably about 0.005% to about 1% by weight, and more preferably about 0.001% to about 0.5% by weight of the solution. Sodium carbonate is a presently preferred pH changing base, and may advantageously be included in an amount of 0.5% by weight of the color changing composition used to make a color changing implement.

Thereafter, the water is removed to form an intermediate device having the pH changing material and dye impregnated within the water absorptive material 10. The pH indicator is thereafter applied using an anhydrous solvent or in some other form that does not include water. Anhydrous solvents that may be used to prevent premature reaction between the pH changing material and pH indicator include, but are not limited to, anhydrous ketones (e.g., acetone and methyl ethyl ketone), esters (e.g., ethyl acetate), lower alkyl alcoholos (e.g., ethyl alcohol, isopropyl alcohol, methyl alcohol, butyl alcohol, and the like), dimethylformamide (DMF), tetrahydrofuran, acetonitrile, mineral spirits, toluene, xylene, and the like. To avoid premature color change, highly hygroscopic solvents such as ethanol and isopropyl alcohol are less advantageous than non-hygroscopic solvents that do not absorb moisture from the air or their environment.

It will be appreciated that the pH indicator could alternatively be applied first using either an aqueous or anhydrous solvent system, either alone or in combination with the dye. The intermediate device formed thereby is then dried to remove the water or other solvent (e.g., by oven drying). Thereafter, the pH changing material can be applied using an anhydrous solvent or other dry form in the absence of water. In many cases, the pH changing material is more hydrophilic and insoluble in organic solvents such that it will usually be preferable in such cases to apply the pH changing material using an aqueous solution prior to applying the anhydrous pH indicator.

The various solutions used to apply the color changing system may be applied by spraying, dipping, or otherwise coating or impregnating the water absorptive material 10. Once the solution has been applied, the material 10 with the applied solutions is dried so as to be substantially free of moisture and other solvents. It may be oven dried or allowed to air dry. The finished endodontic device 20 is illustrated in FIG. 2.

An example of one currently preferred pH indicator is phenolphthalein, which is colorless at neutral pH and below, but that turns red in an alkaline pH range of about 8-10. Examples of other pH indicators that can be used within the scope of the invention include thymolphthalein, which is colorless at a pH below 9 but turns blue in an alkaline pH range of about 9.5-10.5; thymol blue, which changes from yellow to blue within a pH range from about 8 to 9.2; phenol red, which changes from yellow to red within a pH range of about 6.8 to 8.2; bromthymol blue, which changes from yellow to blue within a pH range of about 6 to 7.6; methyl red, which changes from red to yellow within a pH range of about 4.5 to 6.2; bromphenol blue, which changes from yellow to blue within a pH range of about 3 to 4.4; and methyl orange, which changes from red to yellow within a pH range of about 3.1 to 4.3.

It will be appreciated that an appropriate pH changing material should be selected, whether on the basic side or acidic side, depending on the specified working pH range of the pH indicator used. Examples of basic pH changing materials include alkali and alkaline earth metal carbonates (e.g., sodium carbonate), bicarbonates (e.g., sodium bicarbonate), hydroxides (e.g., sodium and potassium hydroxide), and oxides (e.g., calcium oxide). Examples of acidic pH changing materials include carboxylic and other organic acids (e.g., citric, benzoic, fumeric, succinic, malic, maleic, ascorbic, tartaric and the like), mineral acids (e.g., phosphoric), and acidic salts (e.g., aluminum chloride, calcium chloride, ferric chloride, and the like). In addition, a wide range of known buffers can be employed in order to moderate the pH within a desired pH range, such as monosodium phosphate and disodium phosphate.

Examples of dyes that can be employed to impart an initial color to the endodontic device before it is wetted with moisture and/or aqueous sodium hypochlorite include, but are not limited to, any of the known food dyes (e.g., FD&C dyes) and D&C dyes. According to one embodiment, the food dye is susceptible to being bleached by aqueous sodium hypochlorite in order to become colorless in the presence of aqueous sodium hypochlorite found in a root canal. Exemplary food dyes include, but are not limited to, FD&C Blue #1, FD&C Blue #2, FD&C Green #3, FD&C Yellow #5, FD&C Red #3, FD&C Red #40, D&C Green #5, D&C #7, D&C #33, and the like. FD&C Blue #1 and FD&C Green #3 are currently preferred because they are bleached the fastest when exposed to aqueous hypochlorite ions when present in the root canal. That leads to quicker identification of the presence or absence of aqueous hypochlorite.

III. Exemplary Method of Use

In use, when water contacts the endodontic device, the initially dry pH changing material will cause the pH of the water absorbed within the endodontic device to be altered so as to react with the pH indicator to change the color of the device, indicating the presence of moisture within the root canal chamber. According to one embodiment, the device includes a dye that has an initial color (e.g., blue) and a pH indicator (e.g., phenolphthalein) that is initially colorless. The resulting device is initially blue. If no moisture or aqueous sodium hypochlorite is found in the root canal, the device remains blue. If moisture is present, the water causes the pH changing material to interact with the pH indicator to effect a color change (e.g., from blue to purple in the case of a blue dye and a pH indicator that changes from colorless to red). If the water contains sodium hypochlorite, the endodontic device changes to a different color (e.g., white) as at least one of the dye or pH indicator become colorless through bleaching.

Figure 3:
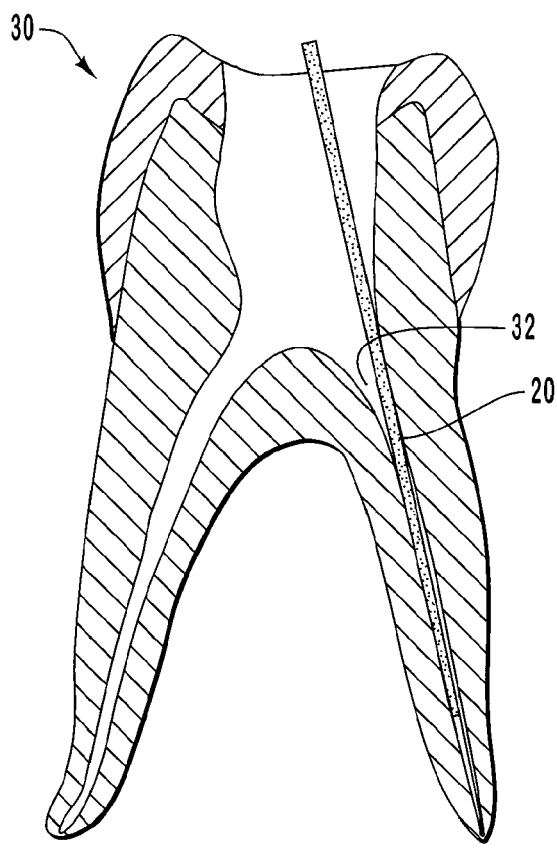
FIG. 3 is a cross sectional view of a patient's tooth with the device of FIG. 2 inserted into the root canal of the tooth.

FIG. 3 illustrates an exemplary tooth 30 where the root canal 32 has been treated using endodontic treatment devices and techniques known in the art. In one embodiment, the root canal 32 is further cleaned and disinfected using an antimicrobial rinse (e.g. an aqueous solution including sodium hypochlorite). Once the root canal 32 has been properly cleaned, the absorptive endodontic device 20 is inserted into the root canal 32 in order to remove any residual moisture. Before inserting the device 20, the device 20 has a first color.

The water absorbing material 10 of the device 20 may be paper, which is sufficiently flexible to allow the device 20 to be inserted through curved areas of the root canal chamber 32. The device 20 is then withdrawn from the root canal 32. A quick visual inspection by the dental practitioner will reveal whether the device has changed color. If moisture is present within the root canal chamber, it will be absorbed by water-absorbing material 10, causing the color changing system that is on or impregnated into the material 10 to change color. In this manner, the device 20 serves both the purpose of removing residual water (and other residual materials such as sodium hypochlorite) from the canal, while also indicating to the dental practitioner whether or not moisture and/or aqueous sodium hypochlorite is present in the root canal 32.

Figure 4:
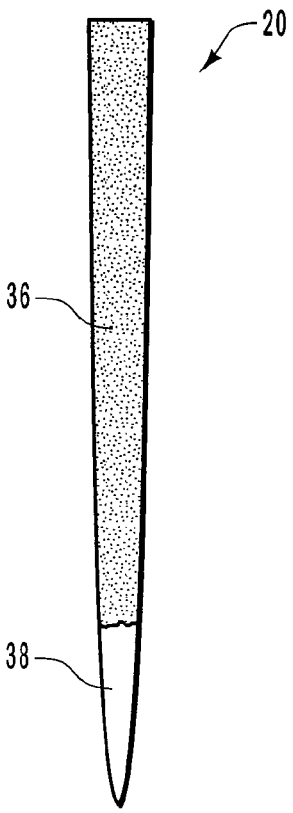
FIG. 4 schematically illustrates the device of FIG. 3 after withdrawing the device from the root canal and observing a color change.

FIG. 4 illustrates the device 20 after having been withdrawn from root canal 32. A proximal portion 36 retains the initial color as it was not contacted with moisture. A distal portion 38 of the device adjacent to the tip 12 has changed color, indicating the presence of moisture and/or sodium hypochlorite within the root canal chamber 32. For example, if the pH indicator is phenolphthalein, the pH changing material is basic, and the dye is blue, it will change from blue (dry condition) to purple (wet condition) if moisture is present in the root canal chamber 32. If sodium hypochlorite is also present in the root canal chamber 32, at least one of the pH indicator or dye will be advantageously bleached to colorless by hypochlorite ion or other aqueous analog, thereby effecting a different color change (e.g., to white). If sodium hypochlorite is present in the root canal 32, it may be desirable to further rinse the root canal 32 with water until no more sodium hypochlorite is detected.

The dental practitioner may continue to insert and withdraw additional devices 20 from the root canal chamber 32 so as to remove any moisture and/or aqueous sodium hypochlorite remaining in the canal 32. When the withdrawn device has the same color as when inserted into the root canal, the dental practitioner knows that the root canal 32 is dry, and may then proceed to seal and/or fill the canal as known in the art.

IV. EXAMPLES OF THE PREFERRED EMBODIMENTS

The following are several examples of color changing systems according to the invention that can be used to manufacture water and sodium hypochlorite indicating devices. The exemplary formulations and manufacturing conditions are given by way of example, and not by limitation, in order to illustrate compositions that have been found to be useful for indicating the presence of water in a root canal. Unless otherwise indicated, all percentages are by weight.

EXAMPLE 1

A pH changing solution used to manufacture water-indicating points according to the invention was made by mixing together the following components:

| | | |
|---|---|---|
| CaO | 0.1% | |
| Water | 99.9% | |

The pH changing solution was sprayed onto a plurality of paper points. The wetted points were then placed into an oven at about 105° C. to dry. The dried, treated paper points were then sprayed with an anhydrous pH sensitive indicator solution made by mixing together the following components:

| | | |
|---|---|---|
| Phenolphthalein | 0.1% | |
| Isopropyl alcohol | 99.9% | |

The wet paper points were again allowed to dry. When wetted with water they turned from white to bright pink. To make a paper point that can also detect the presence of aqueous sodium hypochlorite within a root canal, a dye, such as FD&C Blue #1 is applied to the paper point to give it an initial color when dry. In the presence of moisture, the pH indicator and dye blend to impart a second color to the device. In the presence of sodium hypochlorite, the dye is bleached to yield a device having a third color that results from subtracting the color of the dye.

EXAMPLE 2

A pH changing and dye solution used to manufacture water and sodium hypochlorite indicating points according to the invention was made by mixing together the following components:

| | | |
|---|---|---|
| Deionized water | 98.49% | (e.g., 97.9 to 98.9%) |
| Sodium Carbonate | 1.5% | (e.g., 1.0 to 2.0%) |
| FD&C Blue #1 | 0.01% | (e.g., 0.01 to 0.1%) |

The pH changing solution was applied to a plurality of paper points by dipping the points in the aqueous solution. The wetted points were then placed into a convection oven at about 80° C. to dry. The dried, treated paper points were then dipped into an anhydrous pH indicator solution made by mixing together the following components:

| | | |
|---|---|---|
| Acetone | 99.5% | (e.g., 99.0 to 99.8%) |
| Phenolphthalein | 0.5% | (e.g., 0.2 to 1.0%) |

The wetted paper points were again allowed to dry. The paper points were initially blue as a result of the blue dye. When inserted into a dry root canal, the points remained the same blue color. When wetted with water they turned from blue to purple as the phenolphthalein changed from colorless to red, and red and blue make purple when mixed. When wetted with aqueous sodium hypochlorite, both the dye and pH indicator were bleached, thereby yielding a white point. The bleaching did not occur instantaneously but required up to a half minute or more to impart a definitive fading to white effect.

EXAMPLE 3

Any of the foregoing examples is modified to include bromothymol blue as the pH indicator and citric acid as the pH changing material. The amount of bromothymol blue can be increased or decreased by 0.1% increments until the best color change is noticed. The amount of citric acid can be increased or decreased by 0.1% increments until the best color change is noticed.

EXAMPLE 4

Any of the foregoing examples is modified to include thymol blue as the pH indicator, which changes under basic conditions. The amount of thymol blue can be increased or decreased by 0.1% increments until the best color change is noticed.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An endodontic device for use in determining whether a root canal is dry or whether it contains moisture and/or aqueous sodium hypochlorite, comprising:
    an elongate body formed of a water absorptive material;
    a pH indicator applied to the water absorptive material that changes color in response to being exposed to moisture having a pH within a predetermined pH range;
    a pH changing material applied to the water absorptive material that causes water absorbed into the water absorptive material to have a pH within the predetermined pH range in order to thereby cause the pH indicator to change color when the water absorptive material is exposed to moisture within a root canal; and
    a dye applied to the water absorptive material which differs from the pH indicator and that imparts an initial color to the endodontic device before being exposed to moisture,
    wherein the pH indicator and pH changing material selectively change the endodontic device from the initial color to a second color if moistened with water that is devoid of sodium hypochlorite as a result of an interaction between the pH indicator, water and pH changing material, and wherein at least the dye and optionally the pH indicator is bleached out to colorless so as to change the endodontic device to a third color that differs from the initial color and the second color if moistened with aqueous sodium hypochlorite as a result of a bleaching reaction involving at least the dye and optionally the pH indicator.

2. An endodontic device as recited in claim 1, wherein the water absorptive material comprises paper.

3. An endodontic device as recited in claim 1, wherein the pH indicator comprises phenolphthalein.

4. An endodontic device as recited in claim 1, wherein the pH indicator comprises at least one member selected from the group consisting of thymolphthalein, thymol blue, phenol red, bromthymol blue, methyl red, bromphenol blue, and methyl orange.

5. An endodontic device as recited in claim 1, wherein the pH changing material comprises one or more of an alkali or alkaline earth metal oxide, hydroxide, carbonate, or bicarbonate.

6. An endodontic device as recited in claim 1, wherein the pH changing material comprises one or more of an organic acid, inorganic acid or acidic salt.

7. An endodontic device as recited in claim 1, wherein the dye comprises one or more of FD&C Blue #1, FD&C Blue #2, FD&C Green #3, FD&C Yellow #5, FD&C Red #3, FD&C Red #40, D&C Green #5, D&C #7 or D&C #33.

8. An endodontic device as recited in claim 1, wherein the endodontic device is initially blue but selectively changes to purple when moistened with water or to white when moistened with aqueous sodium hypochlorite for a time sufficient to bleach the pH indicator and dye.

9. An endodontic device for use in determining whether a root canal is dry or whether it contains moisture and/or aqueous sodium hypochlorite, comprising:

an elongate body formed of a water absorptive material;

a pH indicator applied to the water absorptive material that changes color in response to being exposed to moisture having a pH within a predetermined alkaline pH range;

an alkaline pH changing material applied to the water absorptive material that causes water absorbed into the water absorptive material to have a pH within the predetermined alkaline pH range in order to thereby cause the pH indicator to change color when the water absorptive material is exposed to moisture within a root canal; and a pH insensitive and sodium hypochlorite sensitive dye applied to the water absorptive material and that imparts an initial color to the endodontic device before being exposed to moisture, wherein the pH indicator and alkaline pH changing material selectively change the endodontic device from the initial color to a second color if moistened with water that is devoid of sodium hypochlorite as a result of an interaction between the pH indicator, water and alkaline pH changing material, and wherein both the dye and pH indicator are bleached out to colorless so as to selectively change the endodontic device to a third color that differs from the initial color and second color if moistened with aqueous sodium hypochlorite.

10. An endodontic device as recited in claim 9, wherein the pH indicator comprises one or more of phenolphthalein, thymolphthalein, thymol blue, or phenol red and wherein the alkaline pH changing material comprises one or more of an alkali or alkaline earth metal oxide, hydroxide, carbonate, or bicarbonate.

11. An endodontic device for use in determining whether a root canal is dry or whether it contains moisture and/or aqueous sodium hypochlorite, comprising:

an elongate body formed of a water absorptive material;

a pH indicator applied to the water absorptive material that changes color in response to being exposed to moisture having a pH within a predetermined acidic pH range;

an acidic pH changing material applied to the water absorptive material that causes water absorbed into the water absorptive material to have a pH within the predetermined acidic pH range in order to thereby cause the pH indicator to change color when the water absorptive material is exposed to moisture within a root canal; and a pH insensitive and sodium hypochlorite sensitive dye applied to the water absorptive material and that imparts an initial color to the endodontic device before being exposed to moisture, wherein the pH indicator and acidic pH changing material selectively change the endodontic device from the initial color to a second color if moistened with water that is devoid of sodium hypochlorite as a result of an interaction between the pH indicator, water and acidic pH changing material, and wherein both the dye and pH indicator are bleached out to colorless so as to selectively change the endodontic device to a third color that differs from the initial color and second color if moistened with aqueous sodium hypochlorite.

12. An endodontic device as recited in claim 11, wherein the pH indicator comprises one or more of bromthymol blue, methyl red, bromphenol blue, and methyl orange and wherein the acidic pH changing material comprises one or more of phosphoric acid, citric acid, benzoic acid, fumeric acid, succinic acid, malic acid, maleic acid, aluminum chloride, calcium chloride, or ferric chloride.

13. A method of manufacturing an endodontic device for detecting moisture and/or aqueous sodium hypochlorite within a root canal, comprising:

providing an endodontic device formed of a water absorptive material;

applying a pH changing solution that includes a pH changing material to the endodontic device;

drying the endodontic device so as to be substantially free of moisture;

applying an anhydrous pH indicator solution that includes a pH sensitive color changing indicator and an anhydrous volatile solvent to the endodontic device;

drying the endodontic device so as to be substantially dry; and applying a pH insensitive dye to the endodontic device that bleaches out to colorless if moistened with sodium hypochlorite.

14. A method of manufacturing a device as recited in claim 13, wherein the endodontic cone is dried using an oven.

15. A method of manufacturing a device as recited in claim 13, wherein the pH changing solution is an aqueous solution.

16. A method of manufacturing a device as recited in claim 15, wherein the aqueous pH changing solution further includes the pH insensitive dye.

17. A method of manufacturing a device as recited in claim 13, wherein the anhydrous volatile solvent of the pH indicator solution comprises one or more of acetone, isopropyl alcohol, or ethanol.

* * * * *

UNITED STATES PATENT AND TRADEMARK OFFICE
CERTIFICATE OF CORRECTION

| | | |
|---|---|---|
| PATENT NO. | : 8,215,960 B2 | Page 1 of 1 |
| APPLICATION NO. | : 11/533187 | |
| DATED | : July 10, 2012 | |
| INVENTOR(S) | : Wagner et al. | |

It is certified that error appears in the above-identified patent and that said Letters Patent is hereby corrected as shown below:

In the Claims

Column 9
Line 57-58, change "color that differs from the initial color and the second color" to --color, which differs from the initial color and the second color,--

Signed and Sealed this
Fifteenth Day of April, 2014

Michelle K. Lee
*Deputy Director of the United States Patent and Trademark Office*